United States Patent
Taniguchi et al.

(10) Patent No.: US 7,923,572 B2
(45) Date of Patent: Apr. 12, 2011

(54) METHOD FOR PRODUCING KETIMINE STRUCTURE-CONTAINING ALKOXYSILANE

(75) Inventors: Yoshinori Taniguchi, Chiba (JP); Makoto Iwai, Chiba (JP); Keiji Wakita, Midland, MI (US)

(73) Assignee: Dow Corning Toray Company, Ltd., Tokyo (JP)

( * ) Notice: Subject to any disclaimer, the term of this patent is extended or adjusted under 35 U.S.C. 154(b) by 540 days.

(21) Appl. No.: 12/067,746

(22) PCT Filed: Sep. 21, 2006

(86) PCT No.: PCT/JP2006/319230
§ 371 (c)(1),
(2), (4) Date: Mar. 21, 2008

(87) PCT Pub. No.: WO2007/034987
PCT Pub. Date: Mar. 29, 2007

(65) Prior Publication Data
US 2010/0130764 A1 May 27, 2010

(30) Foreign Application Priority Data

Sep. 22, 2005 (JP) .................. 2005-276915

(51) Int. Cl.
*C07F 7/18* (2006.01)
*C08K 5/00* (2006.01)
*C08K 5/5465* (2006.01)
(52) U.S. Cl. ...................... 556/413; 556/424
(58) Field of Classification Search .......... None
See application file for complete search history.

(56) References Cited

U.S. PATENT DOCUMENTS

| 2,942,019 A | 6/1960 | Pike et al. |
| 4,555,561 A | 11/1985 | Sugimori et al. |

FOREIGN PATENT DOCUMENTS

| EP | 0976771 A1 | 2/2000 |
| JP | 03263421 A | 11/1991 |
| JP | 07247294 A | 9/1995 |
| JP | 07247295 A | 9/1995 |
| JP | 2000044817 A | 2/2000 |

OTHER PUBLICATIONS

English language abstract for JP 03263421 extracted from PAJ database, dated Nov. 11, 2008, 9 pages.
English language translation and abstract for JP 07247294 extracted from PAJ database, dated Nov. 11, 2008, 52 pages.
English language translation and abstract for JP 07247295 extracted from PAJ database, dated Nov. 11, 2008, 56 pages.
English language translation and abstract for JP 2000044817 extracted from PAJ database, dated Nov. 11, 2008, 36 pages.
PCT International Search Report for PCT/JP2006/319230, dated Dec. 1, 2006, 3 pages.

*Primary Examiner* — Daniel M Sullivan
*Assistant Examiner* — Yevegeny Valenrod
(74) *Attorney, Agent, or Firm* — Howard & Howard Attorneys PLLC

(57) ABSTRACT

A method for producing ketimine structure-containing alkoxysilane comprising reacting amino-functional alkoxysilane with a monocarbonyl compound by heating and azeotropically distilling off the produced water together with the monocarbonyl compound to yield ketimine structure-containing alkoxysilane, characterized by introducing additional monocarbonyl compound at the time of the azeotropic distillation of the produced water together with the monocarbonyl compound.

8 Claims, No Drawings

METHOD FOR PRODUCING KETIMINE STRUCTURE-CONTAINING ALKOXYSILANE

RELATED APPLICATIONS

This application claims priority to and all the advantages of International Patent Application No. PCT/JP2006/319230, filed on Sep. 21, 2006, which claims priority to Japanese Patent Application No. JP 2005-276915, filed on Sep. 22, 2005.

TECHNICAL FIELD

The present invention relates to a method for producing ketimine structure-containing alkoxysilane and more particularly relates to a low-cost, safe, and convenient method for producing high-purity ketimine structure-containing alkoxysilane in which there remains little of the highly reactive primary amino group originating in the amino-functional alkoxysilane used as a starting material.

BACKGROUND ART

Ketimine structure-containing organoalkoxysilanes are characterized by the fact that the ketimine group is by itself inert to reaction, but reacts readily with water, resulting in decomposition into a monocarbonyl compound and an amino-functional alkoxysilane that contains a highly reactive primary amino group. Ketimine structure-containing organoalkoxysilanes are therefore characterized by an excellent storage stability in the absence of moisture and are useful as adhesion improvers and curing agents for a variety of curable resins and primers.

Dehydration condensation between an amino-functional alkoxysilane and a monocarbonyl compound is described in U.S. Pat. No. 2,942,019 as a method for producing ketimine structure-containing organoalkoxysilane. In this method, however, the alkoxy group undergoes partial hydrolysis and condensation due to the water by-product, resulting in the production of oligomer, that is, organopolysiloxane with a low degree of polymerization (hereinafter DP). This has resulted in a reduced purity for the ketimine structure-containing organoalkoxysilane.

In order to solve this problem, a method is described in Japanese Laid Open Patent Application Number (hereinafter Kokai) Hei 03-263421 in which the water by-product is azeotropically distilled out using a nonpolar organic solvent. A problem with this method has been that the reaction does not go to completion, resulting in large residual amounts of highly reactive amino-functional silane.

A method is described in Kokai Hei 7-247295 in which the water is removed by the addition of a dehydrating agent such as molecular sieve or magnesium sulfate. With this method, however, it has been necessary to run the reaction at low temperatures since water adsorption and desorption are equilibrium reactions, which has resulted in a poor efficiency. Moreover, the alkoxy group undergoes partial hydrolysis and condensation, resulting in a tendency for oligomer to be produced and causing the problem of a low purity for the ketimine structure-containing organoalkoxysilane.

Kokai Hei 7-247294 and 2000-44817 (equivalent to EP096771) describe a method in which the water fraction is azeotropically distilled out while amino-functional alkoxysilane is added dropwise to the heated monocarbonyl compound. However, it has also been difficult with this method to obtain a high-purity ketimine structure-containing organoalkoxysilane product. Particularly in the case of a ketimine structure-containing organoalkoxysilane that bears a highly hydrolyzable alkoxy group such as methoxy, partial hydrolysis and condensation of the methoxysilane with concomitant oligomer production has made it necessary to proceed through an additional distillative purification step in order to raise the purity of such a ketimine structure-containing organoalkoxysilane.

DISCLOSURE OF INVENTION

An object of the present invention is to provide a high-yield method for producing high-purity ketimine structure-containing alkoxysilane in which there remains little of the highly reactive primary amino group originating in the amino-functional silane used as a starting material.

Means Solving the Problems

The method for producing ketimine structure-containing alkoxysilane of the present invention comprising:

reacting an amino-functional alkoxysilane represented by general formula (1)

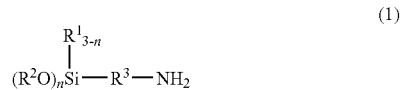

(wherein $R^1$ represents $C_{1-6}$ monovalent hydrocarbyl, $R^2$ represents $C_{1-4}$ alkyl, $R^3$ represents $C_{1-10}$ divalent hydrocarbyl or a divalent organic group represented by $-R^4-NH-R^5-$ (wherein $R^4$ and $R^5$ represent $C_{1-10}$ divalent hydrocarbyl), and n is 1, 2, or 3) with a monocarbonyl compound represented by general formula (2)

(wherein $R^6$ and $R^7$ represent the hydrogen atom or $C_{1-10}$ monovalent hydrocarbyl, but do not simultaneously represent the hydrogen atom) by heating and azeotropically distilling out the produced water along with the monocarbonyl compound to yield ketimine structure-containing alkoxysilane represented by general formula (3)

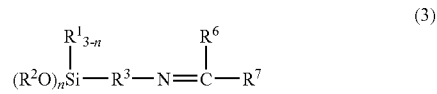

(wherein $R^1$, $R^2$, $R^3$, $R^6$, $R^7$, and n are defined as above), is characterized by introducing additional monocarbonyl compound at the time of the azeotropic distillation of the produced water along with the monocarbonyl compound.

The temperature of the reaction between the monocarbonyl compound and the amino-functional alkoxysilane preferably is at least the temperature of the water/monocarbonyl compound azeotrope and preferably is in a range that does not exceed the boiling point of the monocarbonyl compound. The amount of monocarbonyl compound that is additionally introduced at the time of the azeotropic distillation of the water and monocarbonyl compound is from 1 to 10 moles per 1 mole of the amino-functional alkoxysilane.

The amino-functional alkoxysilane is preferably selected from the group consisting of $(CH_3O)_3Si(CH_2)_3NH_2$, $(CH_3CH_2O)_3Si(CH_2)_3NH_2$, $(CH_3O)_3Si(CH_2)_3NH(CH_2)_2NH_2$, and $(CH_3CH_2O)_3Si(CH_2)_3NH(CH_2)_2NH_2$, and the monocarbonyl compound is preferably methyl isobutyl ketone.

The ketimine structure-containing alkoxysilane of the invention is represented by general formula (4)

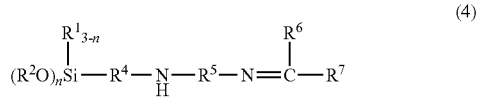

(wherein $R^1$ represents $C_{1-6}$ monovalent hydrocarbyl, $R^2$ represents $C_{1-4}$ alkyl, $R^4$ and $R^5$ represent $C_{1-10}$ divalent hydrocarbyl, $R^6$ and $R^7$ represent $C_{1-10}$ monovalent hydrocarbyl, and n is 1, 2, or 3).

The method according to the present invention for producing ketimine structure-containing alkoxysilane, because it employs the introduction of additional monocarbonyl compound at the time of the azeotropic distillation of water and the monocarbonyl compound, enables the water fraction in the reaction system to be very efficiently distilled out while enabling the concentration ratio between the amino-functional alkoxysilane and the monocarbonyl compound to be held at an ideal ratio during the reaction. This results in rapid completion of the reaction and provides an efficient method. Moreover, purification steps, such as distillative isolation, can be omitted due to the high purity of the obtained ketimine structure-containing alkoxysilane, i.e., there is little production of low DP organopolysiloxane (oligomer) due to partial hydrolysis of the alkoxy group. In particular, high-purity ketimine structure-containing organoalkoxysilane can be obtained even in the production of ketimine structure-containing organoalkoxysilane that contains a highly hydrolyzable alkoxy group such as the methoxy group. In addition, the residual level of the highly reactive primary amino group originating in the starting amino-functional alkoxysilane is extremely low.

The ketimine structure-containing alkoxysilane of the present invention represented by general formula (4) is characterized by its ability to produce a highly reactive primary amine and monocarbonyl compound since the ketimine structure readily undergoes hydrolysis in the presence of moisture. In addition, since the ketimine structure-containing alkoxysilane of the invention also contains secondary amine, it can be expected to provide a higher level of performance as an adhesion promoter, adhesion improver, or curing agent; moreover, additional chemical modification at this secondary amine position is also possible.

BEST MODE FOR CARRYING OUT THE INVENTION

Ketimine structure-containing alkoxysilane is produced according to the present invention by reacting the aforementioned amino-functional alkoxysilane with general formula (1) with the monocarbonyl compound with general formula (2). The amino-functional alkoxysilane used here is shown by general formula (1).

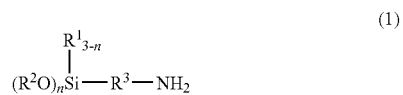

$R^1$ this formula is $C_{1-6}$ monovalent hydrocarbyl and can be exemplified by alkyl such as methyl, ethyl, propyl, and butyl; alkenyl such as vinyl and propenyl; and phenyl. Alkyl is preferred thereamong, and methyl is particularly preferred. $R^2$ is $C_{1-4}$ alkyl such as methyl, ethyl, propyl, butyl, $-CH(CH_3)-CH_3$, $-CH_2-CH(CH_3)-CH_3$, and $-CH(CH_3)-CH_2-CH_3$, wherein methyl or ethyl is preferred. n is 1, 2, or 3.

$R^3$ in general formula (1) is $C_{1-10}$ divalent hydrocarbyl or a divalent organic group represented by $-R^4-NH-R^5-$. The $C_{1-10}$ divalent hydrocarbyl can be exemplified by alkylene such as methylene, ethylene, propylene, butylene, $-(CH_2)_6-$, $-(CH_2)_8-$, $-(CH_2)_{10}-$, and $-CH_2CH(CH_3)-CH_2-$; phenylene; and

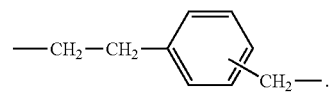

Alkylene is preferred thereamong. The divalent organic group represented by $-R^4-NH-R^5-$ (wherein $R^4$ and $R^5$ represent the same $C_{1-10}$ divalent hydrocarbyl as for the aforementioned $R^3$ and are preferably alkylene) is exemplified by the following.

$-CH_2-CH_2-NH-CH_2-CH_2-NH-CH_2-CH_2-CH_2-$ $-CH_2-CH_2-CH_2-NH-CH_2-CH_2-$

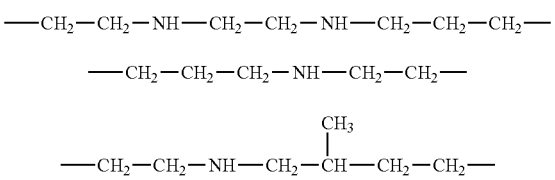

The amino-functional alkoxysilane is specifically exemplified by the following. $(CH_3O)_3Si-CH_2-NH_2$, $(CH_3O)_3Si-(CH_2)_3-NH_2$, $(CH_3O)_3Si-(CH_2)_6-NH_2$, $(CH_3O)_3Si-(CH_2)_{10}-NH_2$, $(CH_3CH_2O)_3-Si-CH_2-NH_2$, $(CH_3CH_2O)_3-Si-(CH_2)_3-NH_2$, $(CH_3CH_2CH_2O)_3-Si-CH_2-NH_2$, $(CH_3CH_2CH_2O)_3-Si-(CH_2)_6-NH_2$, $(CH_3CH_2CH_2CH_2O)_3-Si-CH_2-NH_2$, $(CH_3CH_2CH_2CH_2O)_3-Si-(CH_2)_6-NH_2$,

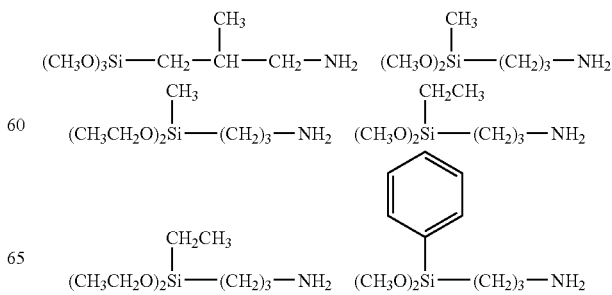

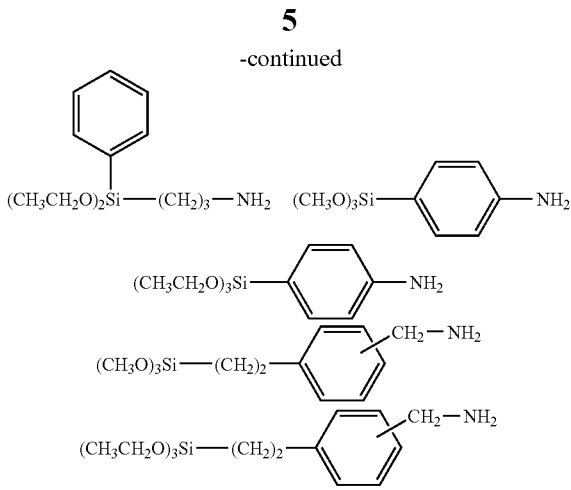

$(CH_3O)_3Si(CH_2)_3NH(CH_2)_2NH_2$, $(CH_3CH_2O)_3Si(CH_2)_3NH(CH_2)_2NH_2$, $(CH_3O)_2(CH_3)Si(CH_2)_3NH(CH_2)_2NH_2$, $(CH_3CH_2O)_2(CH_3)Si(CH_2)_3NH(CH_2)_2NH_2$, $(CH_3O)_2(C_2H_5)Si(CH_2)_3NH(CH_2)_2NH_2$, $(CH_3CH_2O)_2(C_2H_5)Si(CH_2)_3NH(CH_2)_2NH_2$, $(CH_3O)_2(C_6H_5)Si(CH_2)_3NH(CH_2)_2NH_2$, $(CH_3CH_2O)_2(C_6H_5)Si(CH_2)_3NH(CH_2)_2NH_2$.

Preferred among the preceding are the following. $(CH_3O)_3Si(CH_2)_3NH_2$, $(CH_3CH_2O)_3Si(CH_2)_3NH_2$, $(CH_3O)_3Si(CH_2)_3NH(CH_2)_2NH_2$, $(CH_3CH_2O)_3Si(CH_2)_3NH(CH_2)_2NH_2$ The monocarbonyl compound is represented by general formula (2)

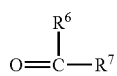

(2)

and the carbonyl group therein forms a ketimine structure by a dehydration reaction with the primary amino group in the aforementioned amino-functional alkoxysilane. $R^6$ and $R^7$ in this formula are $C_{1-10}$ monovalent hydrocarbyl or the hydrogen atom; however, $R^6$ and $R^7$ may not both be the hydrogen atom at the same time. The $C_{1-10}$ monovalent hydrocarbyl can be exemplified by alkyl such as methyl, ethyl, propyl, butyl, and octyl, and aryl such as phenyl and tolyl. In addition, $R^6$ and $R^7$ may be connected to one another with the formation of a ring, in which case $C_{4-10}$ divalent saturated hydrocarbyl is preferred.

The monocarbonyl compound can be specifically exemplified by the following.

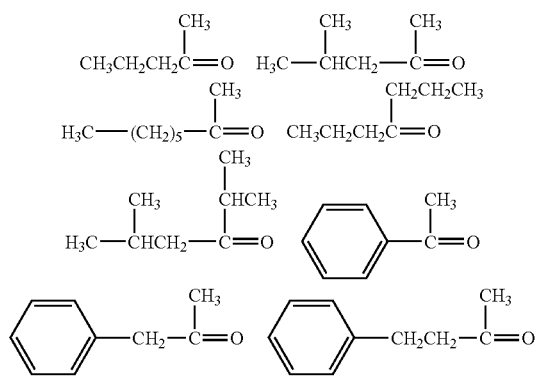

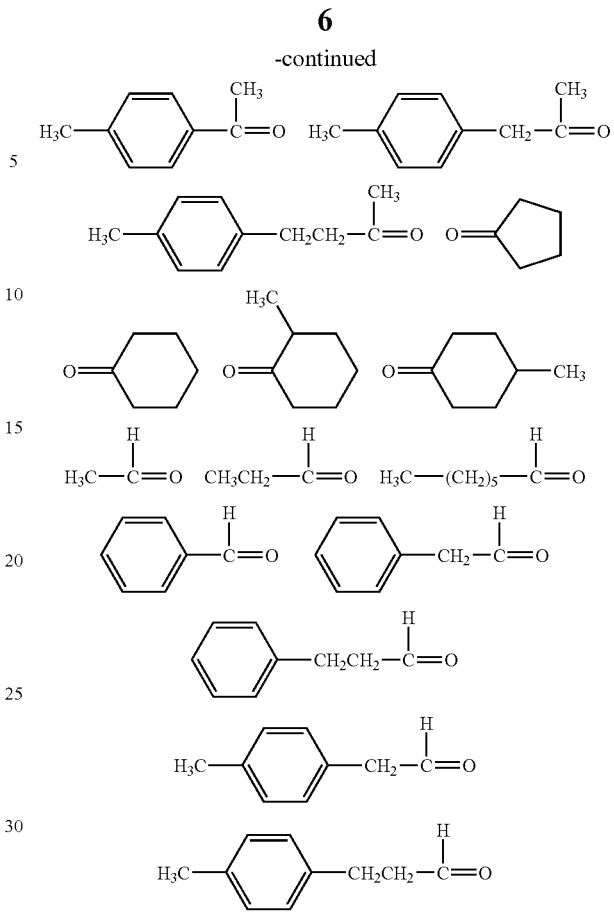

Preferred among the preceding are the following highly hydrophobic monocarbonyl compounds.

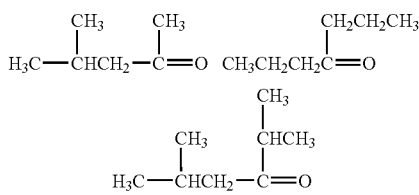

When the monocarbonyl compound is highly hydrophobic, the ability of water to remain in the monocarbonyl compound is diminished, resulting in little water in the reaction system and making possible an inhibition of oligomer production due to water-mediated partial hydrolysis of the alkoxy group.

The ketimine structure-containing alkoxysilane is represented by general formula (3)

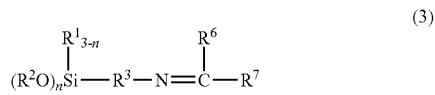

(3)

wherein $R^1$, $R^2$, $R^3$, $R^6$, $R^7$, and n in the formula are defined as above.

Preferred ketimine structure-containing alkoxysilanes are specifically exemplified by the following.

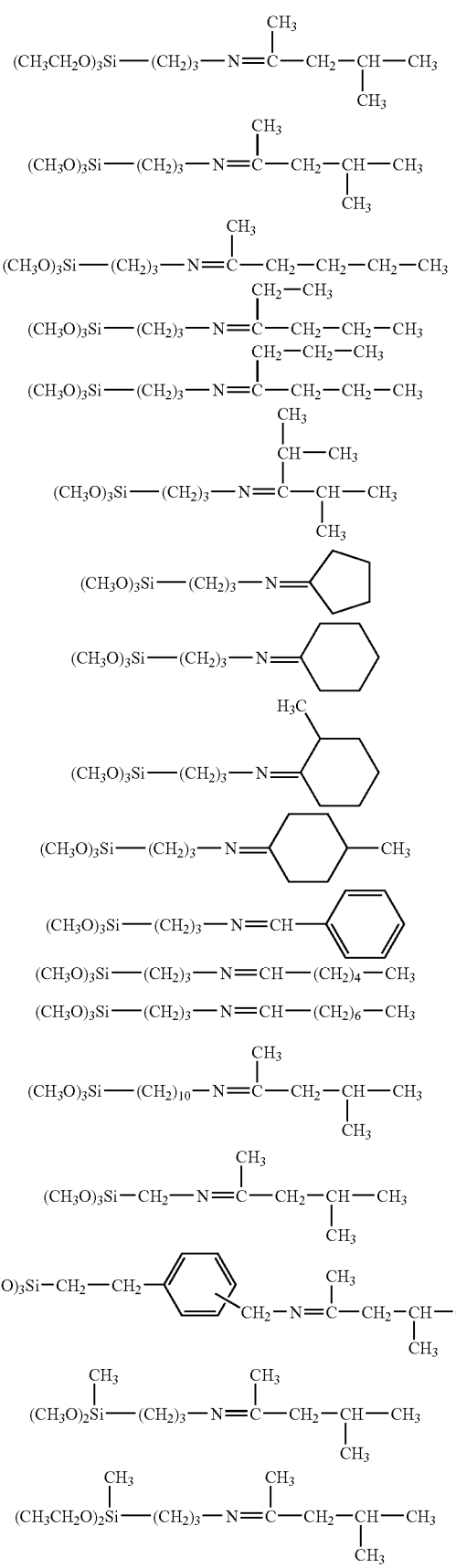

In addition, ketimine structure-containing alkoxysilane with general formula (4)

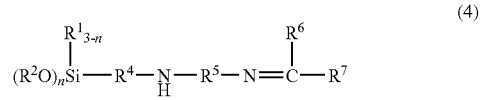

(wherein $R^1$, $R^2$, $R^4$, $R^5$, $R^6$, $R^7$, and n in the formula are defined as above) can be produced, for example, by reacting amino-functional alkoxysilane with the following general formula

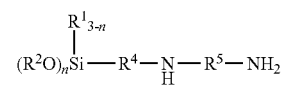

(wherein $R^1$, $R^2$, $R^4$, $R^5$, and n in the formula are defined as above) with the monocarbonyl compound described above. Since the ketimine structure is itself inert, ketimine structure-containing alkoxysilane with general formula (4) is characterized by an excellent storage stability in the absence of moisture. The ketimine structure-containing alkoxysilane with general formula (4) is also characterized by its ability to produce a highly reactive primary amine and monocarbonyl compound since the ketimine structure readily undergoes hydrolysis in the presence of moisture. These characteristic features make the ketimine structure-containing alkoxysilane with general formula (4) useful as an adhesion improver or curing agent for a variety of curable resins and primers. Since the ketimine structure-containing alkoxysilane with general formula (4) also contains secondary amine, it can be expected to provide a higher level of performance as an adhesion promoter, adhesion improver, or curing agent; moreover, additional chemical modification at this secondary amine position is also possible. Based on these features, the ketimine structure-containing alkoxysilane with general formula (4) is useful as an adhesion promoter or curing agent for incorporation into various primer compositions and single-package curable resins, e.g., epoxy resins, urethane resins, phenolic resins, and so forth. Preferred ketimine structure-containing alkoxysilanes with general formula (4) can be exemplified by the following.

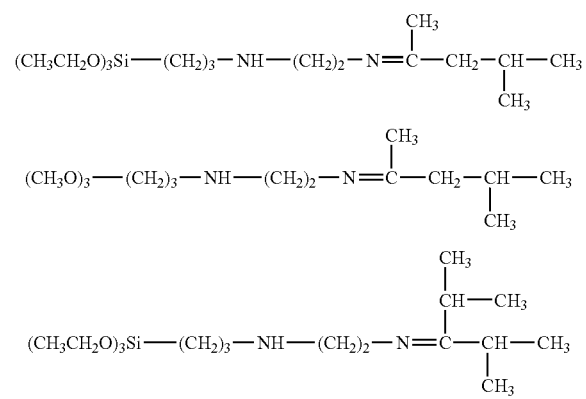

-continued

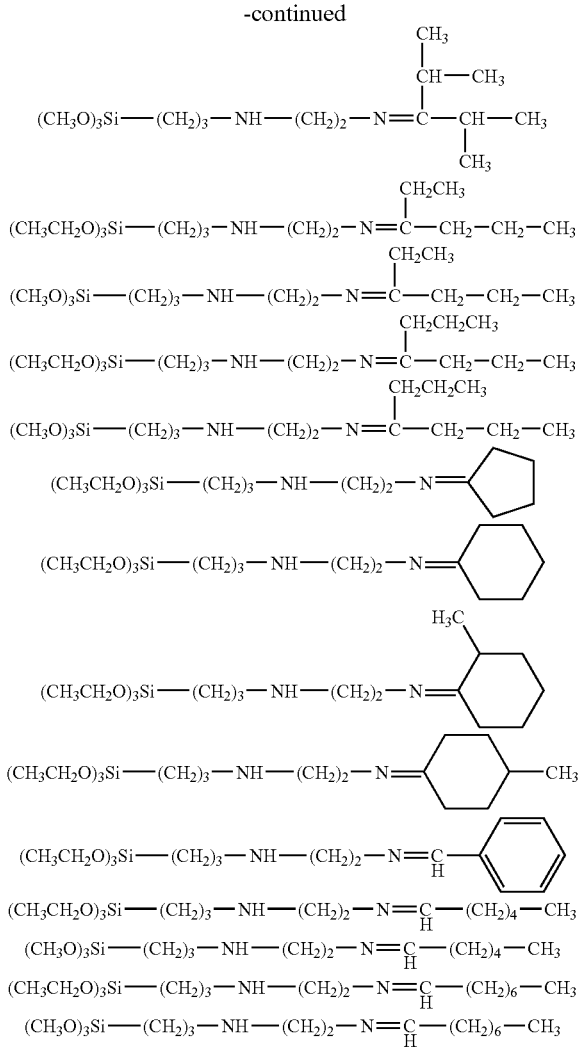

Preferred thereamong are the following.

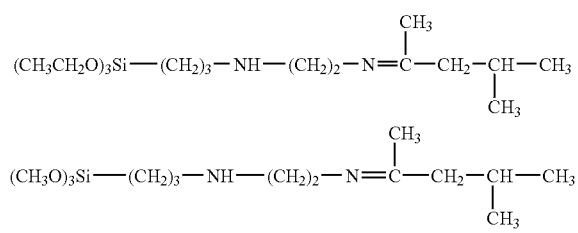

The method according to the present invention for producing ketimine structure-containing alkoxysilane is a method that obtains a ketimine structure-containing alkoxysilane by reacting an amino-functional alkoxysilane and a monocarbonyl compound under heating and azeotropically distilling out the produced water together with the monocarbonyl compound; the instant method is characterized by the additional introduction of monocarbonyl compound at the time of the azeotropic distillation of the produced water along with the monocarbonyl compound. The molar ratio at which the amino-functional alkoxysilane and the monocarbonyl compound are mixed prior to the start of the water/monocarbonyl compound azeotropic distillation is preferably in the range of 1.5 to 10 moles and more preferably 3.0 to 10 moles of the monocarbonyl compound per 1 mole of the amino-functional alkoxysilane. Highly reactive primary amino group originating in the starting amino-functional alkoxysilane readily remains in the final product when the number of moles of monocarbonyl compound per 1 mole of the amino-functional alkoxysilane falls below the aforementioned range. When the aforementioned range is exceeded, the pot yield during production is too low, which is disadvantageous from a cost perspective.

While any method can be used to introduce the amino-functional alkoxysilane and monocarbonyl compound into the reaction apparatus, introduction is preferably carried out in such a manner that the aforementioned molar ratio range between the amino-functional alkoxysilane and monocarbonyl compound is not violated. In addition, either or both of the amino-functional alkoxysilane and monocarbonyl compound may be preheated and then introduced into the reaction apparatus. When a starting material is preheated, the temperature is preferably within the range of appropriate reaction temperatures as described below.

The reaction between the amino-functional alkoxysilane and monocarbonyl compound is carried out under the application of heat. In a preferred embodiment, the reaction temperature is quickly adjusted, after the amino-functional alkoxysilane and monocarbonyl compound have been introduced into the reaction apparatus, to at least the temperature of the water/monocarbonyl compound azeotrope, but not above the boiling point of the monocarbonyl compound. When the reaction temperature is below the temperature of the water/monocarbonyl compound azeotrope, the water produced by the reaction of the amino-functional alkoxysilane and monocarbonyl compound is not distilled out and remains in the system, which promotes water-induced partial hydrolysis of the amino-functional alkoxy group and thereby increases the amount of oligomer produced, resulting in a reduced purity. When, on the other hand, the reaction temperature is higher than the boiling point of the monocarbonyl compound, the concentration of the monocarbonyl compound undergoes a sharp decline and the efficiency at which the water is azeotropically distilled out with the monocarbonyl compound undergoes a decline, which can result in promotion of the water-induced hydrolysis of the amino-functional alkoxy group, finally resulting in an increase in the amount of oligomer produced.

The reaction temperature under consideration will vary as a function of the pressure within the reaction apparatus and the type of monocarbonyl compound. For example, when the reaction is run at ambient pressure and the monocarbonyl compound is methyl isobutyl ketone, the reaction temperature can be 80 to 130° C. since the methyl isobutyl ketone/water azeotrope temperature is approximately 80° C. and the boiling point of methyl isobutyl ketone is 130° C. When the monocarbonyl compound is methyl ethyl ketone and the reaction is run at ambient temperature, the reaction temperature can be 73 to 80° C. since the methyl ethyl ketone/water azeotrope temperature is approximately 73° C. and the boiling point of methyl ethyl ketone is 80° C.

The method according to the present invention for producing ketimine structure-containing alkoxysilane is characterized by the additional introduction of the monocarbonyl compound at the time the water produced in the reaction is azeotropically distilled out along with the monocarbonyl compound. The introduction of the monocarbonyl compound at the time of the azeotropic distillation of water and the monocarbonyl compound is preferably started immediately after azeotropic distillation has started. The start of azeotropic distillation of water and the monocarbonyl compound can be confirmed visually or by the fact that the temperature of the vapor phase in the reaction apparatus has reached the temperature of the water/monocarbonyl compound azeotrope.

The amount of fresh monocarbonyl compound introduced at the time of the water/monocarbonyl compound azeotropic distillation is not particularly limited, but the range of 1.0 to 10 moles monocarbonyl compound per 1 mole amino-functional alkoxysilane is preferred and the range of 3.0 to 7.0 moles monocarbonyl compound per 1 mole amino-functional alkoxysilane is more preferred. When the amount of monocarbonyl compound introduced at the time of the water/monocarbonyl compound azeotropic distillation is below the lower limit given above, azeotropic distillation of the water and monocarbonyl compound becomes insufficient, which can result in water-induced partial hydrolysis of the alkoxy group, promotion of oligomer production, and a reduction in purity. When, on the other hand, the amount of monocarbonyl compound introduced at the time of the water/monocarbonyl compound azeotropic distillation exceeds the upper limit given above, too much time is required to introduce the monocarbonyl compound and distill off the excess monocarbonyl compound, which can result in the appearance of secondary reactions and can be disadvantageous from a cost perspective.

The method for introducing the monocarbonyl compound at the time of the water/monocarbonyl compound azeotropic distillation is not particularly limited, but it is preferably directly introduced into the solution in order to carry out the water/monocarbonyl compound azeotropic distillation at good efficiency.

The rate of monocarbonyl compound introduction at the time of the water/monocarbonyl compound azeotropic distillation is not particularly limited, but it is preferably adjusted in such a manner that the rate of discharge of the azeotrope component from the system is equal to the rate of introduction of the monocarbonyl compound. The reasons for this are as follows. When the rate of monocarbonyl compound introduction at the time of the water/monocarbonyl compound azeotropic distillation is too fast, the temperature within the reaction apparatus ends up declining and the efficiency of water/monocarbonyl compound azeotropic distillation therefore declines, which can result in water-induced partial hydrolysis of the alkoxy group, promotion of oligomer production, and a decline in purity. When the rate of monocarbonyl compound introduction at the time of the water/monocarbonyl compound azeotropic distillation is too slow, the rapid discharge of the monocarbonyl compound from the system by the azeotropic distillation will cause the concentration of the amino-functional alkoxysilane in the reaction apparatus to undergo a relative increase with respect to the monocarbonyl compound, which can result in, for example, a failure of the reaction to go to completion and a decline in the efficiency of the water/monocarbonyl compound azeotropic distillation, leading to water-induced partial hydrolysis of the alkoxy group, promotion of oligomer production, and a reduction in purity.

The reaction between the amino-functional alkoxysilane and monocarbonyl compound is preferably run under an inert gas such as nitrogen or argon. In addition, the water fraction in the starting amino-functional alkoxysilane and monocarbonyl compound is also preferably as small as possible. The water fraction in the monocarbonyl compound freshly introduced at the time of the water/monocarbonyl compound azeotropic distillation is also preferably as small as possible.

The azeotropic mixture distilled out of the reaction apparatus is a mixture that contains alcohol, water, and, as its major component, the monocarbonyl compound. Since the water and alcohol can be conveniently and safely removed using a dehydrating agent such as, for example, molecular sieve, the monocarbonyl compound can be easily regenerated and re-used.

Organic solvent lacking active hydrogen, for example, toluene, xylene, benzene, hexane, ethylene chloride, chloroform, trichloroethylene, or cyclohexane, may optionally be used as a reaction solvent. However, all of these are weakly polar solvents, which results in a diminished reaction efficiency between the amino-functional alkoxysilane and monocarbonyl compound thereby making it possible for highly reactive primary amino group originating in the amino-functional alkoxysilane to remain present; it is therefore preferred that these organic solvents not be used.

EXAMPLES

The present invention is described in greater detail in the examples provided below. % in the examples refers to mass %.

Example 1

300 g (3.0 mol) methyl isobutyl ketone and 179.0 g (1.0 mol) 3-aminopropyltrimethoxysilane were introduced into a 1-liter 4-neck flask equipped with a nitrogen gas inlet tube, a thermometer, a Dean-Stark water trap, a Dimroth condenser, and a dropping funnel and were heated with stirring.

At 30 minutes after the start of heating and stirring, the liquid layer temperature in the flask had reached 82° C. and, because it was confirmed visually that a reflux of methyl isobutyl ketone and water product had begun, azeotropic distillation was begun. At the same time that this azeotropic distillation was begun, the dropwise addition of 300 g (3.0 mol) methyl isobutyl ketone, which had been weighed into the dropping funnel in advance, was also begun. This dropwise addition of methyl isobutyl ketone required about 2 hours, during which time the dropwise addition of methyl isobutyl ketone was carried out at a rate such that the amount of liquid in the 4-neck flask remained constant. In addition, the reflux temperature rose during this dropwise addition, finally reaching 118° C., the reflux temperature of methyl isobutyl ketone. Azeotropic distillation was halted when the dropwise addition was finished and cooling was carried out. Immediately thereafter, the remaining unreacted methyl isobutyl ketone was distilled out under reduced pressure at 60° C., yielding a weakly yellow, transparent liquid.

The results of analysis by $^{13}$C-nuclear magnetic resonance spectroscopic analysis, infrared spectroscopic analysis, and GC-MS analysis confirmed that this weakly yellow, transparent liquid was a compound with the formula

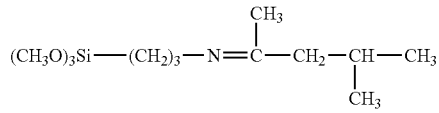

and the hydrolyzate thereof. The purity of the ketimine structure-containing alkoxysilane was 95.4% according to analysis by $^{29}$Si-nuclear magnetic resonance spectroscopy. Based on the primary amine content according to $^{13}$C-nuclear magnetic resonance spectroscopic analysis, the conversion thereof was determined to be 99.1%.

Comparative Example 1

An experiment was run as in Example 1, but without carrying out the dropwise addition of methyl isobutyl ketone that was carried out in Example 1 after the start of azeotropic distillation. A transparent yellow liquid was obtained. The conversion and purity were determined as in Example 1 and are reported in Table 1.

Examples 2, 3, and 4

Experiments were carried out as in Example 1, but using the amino-functional alkoxysilanes reported in Table 1 rather than the γ-aminopropyltrimethoxysilane used in Example 1. The conversion and purity were determined as in Example 1 and are reported in Table 1.

Comparative Examples 2, 3, and 4

Experiments were carried out as in Comparative Example 1, but using the amino-functional alkoxysilanes reported in Table 1 rather than the γ-aminopropyltrimethoxysilane used in Comparative Example 1. The conversion and purity were determined as in Example 1 and are reported in Table 1.

Example 5

The methyl isobutyl ketone/water azeotrope component distilled out during the reaction in Example 1 came to 323 g. This azeotrope component was transferred to a 1-liter recovery flask; 20 g molecular sieve was added (type 4A, 1/13); and regeneration was carried out by dehydration for 24 hours at room temperature. An experiment was carried out as in Example 2, but using this regenerated methyl isobutyl ketone, yielding a light yellow, transparent liquid. The conversion and purity were determined as in Example 1 and are reported in Table 1.

Comparative Example 5

500 g (5.0 mol) methyl isobutyl ketone was introduced into a 1-liter 4-neck flask equipped with a nitrogen gas inlet tube, a thermometer, a Dean-Stark water trap, a Dimroth condenser, and a dropping funnel, and 179 g (1.0 mol) 3-aminopropyltrimethoxysilane was then added dropwise over 3 hours at 118° C. At 10 minutes after the start of dropwise addition, the start of reflux by the water product and methyl isobutyl ketone was visually confirmed, and azeotropic distillation was therefore started. The reflux temperature rose during dropwise addition and ultimately reached 135° C. Azeotropic distillation was stopped upon completion of dropwise addition and the remaining unreacted methyl isobutyl ketone was immediately distilled out at 90° C. under reduced pressure, yielding a weakly yellow, transparent liquid.

The results of analysis by $^{13}$C-nuclear magnetic resonance spectroscopic analysis, infrared spectroscopic analysis, and GC-MS analysis confirmed that this weakly yellow, transparent liquid was a compound with the formula

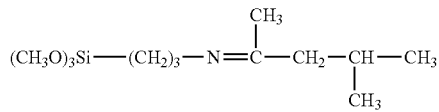

and the hydrolyzate thereof. The purity of the ketimine structure-containing alkoxysilane was 12.4% according to analysis by $^{29}$Si-nuclear magnetic resonance spectroscopy. Based on the primary amine content according to $^{13}$C-nuclear magnetic resonance spectroscopic analysis, the conversion thereof was determined to be 98.6%.

TABLE 1

|  | amino group-containing alkoxysilane | conversion (%) | purity (%) |
|---|---|---|---|
| Example 1 | 3-aminopropyltrimethoxysilane | 99.1 | 95.4 |
| Comp. Ex. 1 |  | 98.7 | 2.1 |
| Example 2 | 3-aminopropyltriethoxysilane | 99.5 | 95.8 |
| Comp. Ex. 2 |  | 98.2 | 19.9 |
| Example 3 | aminoethylaminopropyltrimethoxysilane | 97.6 | 62.8 |
| Comp. Ex. 3 |  | 98.1 | <1.0 |
| Example 4 | aminoethylaminopropyltrimethoxysilane | 98.5 | 50.2 |
| Comp. Ex. 4 |  | 97.7 | <1.0 |
| Example 5 | 3-aminopropyltrimethoxysilane | 99.1 | 96.0 |
| Comp. Ex. 5 | 3-aminopropyltrimethoxysilane | 98.6 | 12.4 |

INDUSTRIAL APPLICABILITY

Ketimine structure-containing alkoxysilane afforded by the production method according to the present invention exhibits a high reaction product purity and also contains very low residual levels of the highly reactive primary amino group originating with the starting amino-functional alkoxysilane. As a consequence, when this ketimine structure-containing alkoxysilane is incorporated as an adhesion promoter, adhesion improver, or curing agent in any of various primers or curable resins, e.g., epoxy resins, urethane resins, and so forth, it can be expected to raise the adhesiveness without impairing the fluidity or storage stability of the resin.

Among ketimine structure-containing alkoxysilanes afforded by the production method according to the present invention, ketimine structure-containing alkoxysilanes with the following general formula

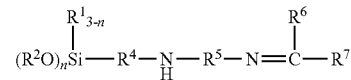

(wherein $R^1$ represents $C_{1-6}$ monovalent hydrocarbyl, $R^2$ represents $C_{1-4}$ alkyl, $R^4$ and $R^5$ represent $C_{1-10}$ divalent hydrocarbyl, $R^6$ and $R^7$ represent $C_{1-10}$ monovalent hydrocarbyl, and n is 1, 2, or 3), because they contain secondary amine, can be expected to provide an even higher degree of adhesiveness. In addition, the execution of additional chemical modification at the secondary amine position is also a possibility.

The invention claimed is:
1. A method for producing ketimine structure-containing alkoxysilane comprising;
reacting an amino-functional alkoxysilane represented by general formula (1)

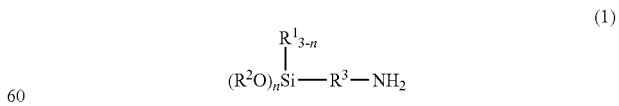

(1)

(wherein $R^1$ represents $C_{1-6}$ monovalent hydrocarbyl, $R^2$ represents $C_{1-4}$ alkyl, $R^3$ represents $C_{1-10}$ divalent hydrocarbyl or a divalent organic group represented by —$R^4$—NH—$R^5$— (wherein $R^4$ and $R^5$ represent $C_{1-10}$ divalent hydrocarbyl), and n is 1, 2, or 3) with a monocarbonyl compound represented by general formula (2)

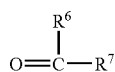
(2)

(wherein $R^6$ and $R^7$ represent the hydrogen atom or $C_{1-10}$ monovalent hydrocarbyl, but do not simultaneously represent the hydrogen atom) by heating and azeotropically distilling off the produced water along with the monocarbonyl compound to yield ketimine structure-containing alkoxysilane represented by general formula (3)

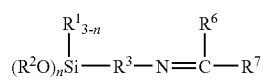
(3)

(wherein $R^1$, $R^2$, $R^3$, $R^6$, $R^7$, and n are defined as above), characterized by introducing additional monocarbonyl compound at the time of the azeotropic distillation of the produced water along with the monocarbonyl compound of formula (2).

2. The method according to claim 1 for producing ketimine structure-containing alkoxysilane, wherein the amount of monocarbonyl compound that is additionally introduced at the time of the azeotropic distillation of the produced water along with the monocarbonyl compound is from 1 to 10 moles per 1 mole of the amino-functional alkoxysilane.

3. The method according to claim 1 for producing ketimine structure-containing alkoxysilane, characterized in that the temperature of the reaction between the monocarbonyl compound and the amino-functional alkoxysilane is at least the temperature of the water/monocarbonyl compound azeotrope and is in a range that does not exceed the boiling point of the monocarbonyl compound.

4. The method according to claim 1 for producing ketimine structure-containing alkoxysilane, characterized in that the amino-functional alkoxysilane is selected from the group consisting of $(CH_3O)_3Si(CH_2)_3NH_2$, $(CH_3CH_2O)_3Si(CH_2)_3NH_2$, $(CH_3O)_3Si(CH_2)_3NH(CH_2)_2NH_2$, and $(CH_3CH_2O)_3Si(CH_2)_3NH(CH_2)_2NH_2$.

5. The method according claim 1 for producing ketimine structure-containing alkoxysilane, characterized in that the monocarbonyl compound is methyl isobutyl ketone.

6. The method according to claim 2 for producing ketimine structure-containing alkoxysilane, characterized in that the monocarbonyl compound is methyl isobutyl ketone.

7. The method according to claim 3 for producing ketimine structure-containing alkoxysilane, characterized in that the monocarbonyl compound is methyl isobutyl ketone.

8. The method according to claim 4 for producing ketimine structure-containing alkoxysilane, characterized in that the monocarbonyl compound is methyl isobutyl ketone.

\* \* \* \* \*